United States Patent
Monfray et al.

(10) Patent No.: US 8,878,258 B2
(45) Date of Patent: Nov. 4, 2014

(54) DETECTOR OF BIOLOGICAL OR CHEMICAL MATERIAL AND CORRESPONDING ARRAY OF DETECTORS

(75) Inventors: Stéphane Monfray, Eybens (FR); Thomas Skotnicki, Crolles-Montfort (FR)

(73) Assignee: STMicroelectronics (Crolle 2) SAS, Crolles (FR)

( * ) Notice: Subject to any disclaimer, the term of this patent is extended or adjusted under 35 U.S.C. 154(b) by 89 days.

(21) Appl. No.: 12/914,033

(22) Filed: Oct. 28, 2010

(65) Prior Publication Data
US 2011/0108892 A1 May 12, 2011

(30) Foreign Application Priority Data
Oct. 30, 2009 (FR) ........................................ 09 57688

(51) Int. Cl.
*G01N 27/403* (2006.01)
*H01L 21/00* (2006.01)
*G01N 33/543* (2006.01)
*G01N 27/414* (2006.01)

(52) U.S. Cl.
CPC ........ *G01N 27/414* (2013.01); *G01N 33/54373* (2013.01); *G01N 33/5438* (2013.01)
USPC ........................................... 257/253; 438/49

(58) Field of Classification Search
USPC .............. 257/253, 347–354; 438/49
See application file for complete search history.

(56) References Cited

U.S. PATENT DOCUMENTS

| 4,849,798 | A |   | 7/1989  | Wantanabe |
|-----------|---|---|---------|-----------|
| 5,466,348 | A | * | 11/1995 | Holm-Kennedy ............ 205/775 |
| 5,827,482 | A | * | 10/1998 | Shieh et al. ................ 422/82.02 |
| 6,203,981 | B1| * | 3/2001  | Ackley et al. ................ 435/6.11 |
| 2002/0142624 | A1 | * | 10/2002 | Levy et al. ..................... 438/786 |
| 2003/0045053 | A1 | * | 3/2003  | Tsuzumitani et al. ........ 438/243 |
| 2004/0007740 | A1 | * | 1/2004  | Abstreiter et al. ............ 257/347 |
| 2004/0185591 | A1 |   | 9/2004  | Hsiung et al. |
| 2005/0053524 | A1 | * | 3/2005  | Keersmaecker et al. ....... 422/88 |
| 2007/0295988 | A1 | * | 12/2007 | Yamamoto et al. ........... 257/147 |
| 2008/0012007 | A1 |   | 1/2008  | Li et al. |
| 2008/0094074 | A1 |   | 4/2008  | Kim et al. |
| 2008/0258179 | A1 | * | 10/2008 | Tour et al. ..................... 257/253 |
| 2009/0014757 | A1 | * | 1/2009  | Takulapalli et al. .......... 257/253 |
| 2009/0267057 | A1 |   | 10/2009 | Setayesh et al. |

FOREIGN PATENT DOCUMENTS

EP 1348951 A1 10/2003
WO WO 2009/007543 A1 6/2009

OTHER PUBLICATIONS

French Search Report dated Oct. 30, 2010 from corresponding French Application No. 09/57688.

* cited by examiner

*Primary Examiner* — Karen Kusumakar
(74) *Attorney, Agent, or Firm* — Seed IP Law Group PLLC

(57) ABSTRACT

A detector of biological or chemical material, including a MOS transistor having its channel region inserted between upper and lower insulated gates, the upper insulated gate including a detection layer capable of generating a charge at the interface of the upper insulated gate and of its gate insulator, the thickness of the upper gate insulator being smaller than the thickness of the lower gate insulator.

33 Claims, 1 Drawing Sheet

DETECTOR OF BIOLOGICAL OR CHEMICAL MATERIAL AND CORRESPONDING ARRAY OF DETECTORS

CROSS REFERENCE TO RELATED APPLICATIONS

This application claims the priority benefit of French patent application number 09/57688, filed on Oct. 30, 2009, entitled "DETECTOR OF BIOLOGICAL OR CHEMICAL MATERIAL AND CORRESPONDING ARRAY OF DETECTORS," which is hereby incorporated by reference to the maximum extent allowable by law.

BACKGROUND OF THE INVENTION

1. Field of the Invention

The present invention relates to the field of integrated circuits. It more specifically relates to the detection of biological or chemical material.

2. Discussion of the Related Art

To detect the presence of biological or chemical material in an environment and quantify its concentration, the use of a detector formed of a semiconductor chip coated with a layer of a material capable of bonding to the biological or chemical material has been provided.

FIG. 1 shows such a detector 1 arranged in an aqueous environment 2. Aqueous environment 2 contains molecules 4 with a concentration in medium 2 which is desired to be quantified. Detector 1 is a MOS transistor comprising source and drain regions 6 and 8, as well as a gate layer 10 and a gate insulator 12. Insulated gate 10 is a detection layer comprising dangling bonds 14.

When a molecule 4 pairs with a dangling bond 14, an electric charge 15 appears in gate layer 10. The appearing of electric charge 15 generates an electrically opposite charge 17 in channel region 18 of transistor 1, gate 10 being further biased to a voltage $V_p$ close to the transistor threshold voltage. The generation of charge 17 modifies the gate voltage of transistor 1, and thus its source-drain current. Quantifying this modification enables to deduce the concentration of molecules 4 in medium 2.

Such a detector 1 requires the presence of an external electrode enabling to bias gate 10 to voltage $V_p$. The reproducibility and the reliability of the concentration measurements are not guaranteed. Further, the sensitivity level of such a detector is not sufficient. When there is a small amount of material to be detected, the voltage difference generated by the appearing of charges 17 does not enable to sufficiently modify the gate voltage of the transistor.

SUMMARY OF THE INVENTION

An object of an embodiment of the present invention is to provide a detector of biological or chemical material avoiding at least some of the disadvantages of prior art detectors.

A more specific object of an embodiment of the present invention is to provide a detector capable of performing reliable and repeatable measurements of the concentration of biological or chemical material.

Another object of an embodiment of the present invention is to provide a self-contained detector integrated in a semiconductor substrate.

Thus, an embodiment of the present invention provides a detector of biological or chemical material, comprising a MOS transistor having its channel region inserted between upper and lower insulated gates, the upper insulated gate comprising a detection layer capable of generating a charge at the interface of the upper insulated gate and of its gate insulator, the thickness of the upper gate insulator being smaller than the thickness of the lower gate insulator.

According to another embodiment of the present invention, the ratio between the thickness of the lower gate insulator and the thickness of the upper gate insulator ranges between 2 and 20, preferably between 8 and 10.

According to another embodiment of the present invention, the thickness of the upper gate insulator ranges between 0.5 and 5 nm, preferably between 2 and 3 nm.

According to another embodiment of the present invention, the thickness of the lower gate insulator ranges between 5 and 50 nm, preferably between 15 and 25 nm.

According to another embodiment of the present invention, the thickness of the channel region is defined so that the upper and lower gates are capacitively coupled.

According to another embodiment of the present invention, the thickness of the channel region ranges between 1 and 40 nm, preferably between 2 and 20 nm.

According to another embodiment of the present invention, the lower insulated gate is electrically connected to a contact electrode arranged on the front surface.

According to another embodiment of the present invention, the lower gate is formed of a heavily-doped well connected to the contact electrode by a sink.

Another embodiment of the present invention provides an array of detectors comprising a plurality of detectors such as described hereabove.

According to another embodiment of the present invention, at least two detectors comprise a different detection layer.

The foregoing objects, features, and advantages of the present invention will be discussed in detail in the following non-limiting description of specific embodiments in connection with the accompanying drawings.

DETAILED DESCRIPTION

Figure 1:
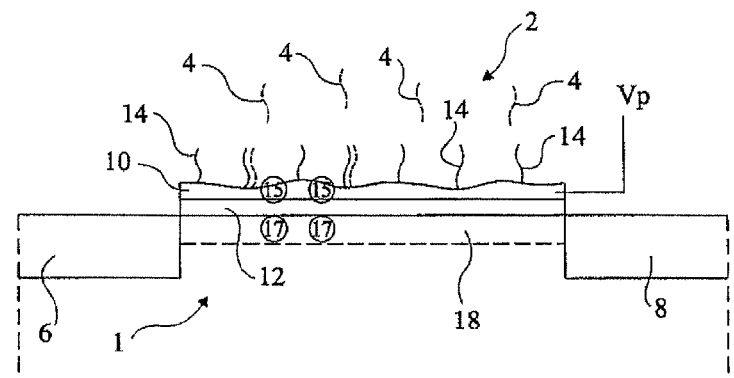
FIG. 1, previously described, is a simplified cross-section view of detector.

For clarity, the same elements have been designated with the same reference numerals in the different drawings and, further, as usual in the representation of integrated circuits, the various drawings are not to scale.

Figure 2:
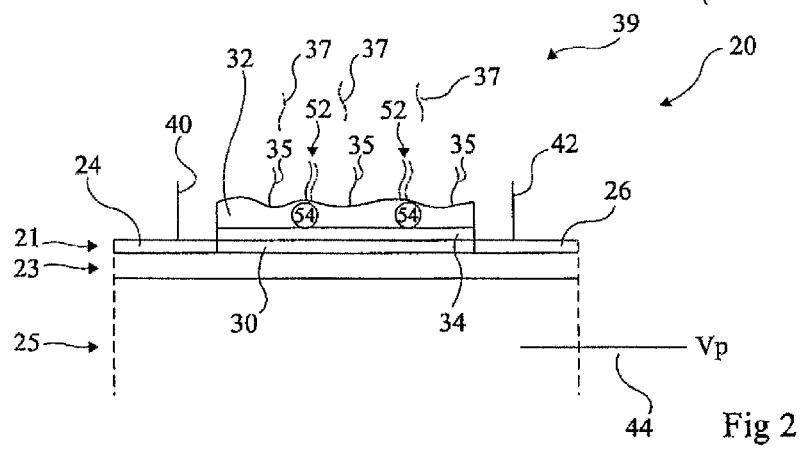
FIG. 2 is a simplified cross-section view of a detector according to another embodiment of the present invention.

FIG. 2 is a simplified view showing a detector 20 manufactured in a semiconductor substrate of SOI type (Silicon On Isolator) comprising a thin single-crystal silicon layer 21 on an insulating layer 23, for example, silicon oxide, laid on a silicon wafer 25. A MOS transistor comprising respective source and drain regions 24 and 26 on either side of a channel region 30 is formed in a portion of layer 21. A gate insulator 34 is arranged above channel region 30. An upper insulated gate 32 is arranged on insulator 34. As an example, gate insulator 34 may be made of silicon oxide. Wafer 25 forms a lower insulated gate of the transistor, insulating layer 23 forming a lower gate insulator.

Upper insulated gate 32 is formed of a detection layer comprising dangling bonds 35. Bonds 35 are capable of pairing with molecules 37 present in a medium 39 in which detector 20 can be placed.

Source and drain regions 24 and 26 are respectively connected to contact electrodes 40 and 42. Similarly, the lower insulated gate is electrically connected to a contact electrode 44.

In operation, the lower insulated gate is biased to a voltage $V_p$ close to the threshold voltage of MOS transistor 24-30-26. When a voltage is applied between respective source and drain electrodes 40 and 42, a low source-drain current appears due to the biasing of the lower gate to a voltage close to the threshold voltage of the transistor.

When detector 20 is placed in medium 39, molecules 37 of the medium are likely to pair with dangling bonds 35 of upper insulating gate 32. As an example, FIG. 2 shows two couples 52, each formed of a molecule 37 associated with a dangling bond 35. The pairing step causes the generation of an electric charge 54 in gate 32, at the interface between the gate and gate insulator 34. Due to the resulting gate voltage, the transistor is made more or less conductive, according to the biasing of the induced charge. Measuring the variation of the source-drain current provides the concentration of molecules 37 in medium 39.

According to a feature of the present invention, the thickness of gate insulator 34 is selected to be as small as possible. As an example, the thickness of insulator 34 ranges between 0.5 and 5 nm, preferably between 2 and 3 nm. Detector 20 thus is very sensitive to the appearing of charges 54. The variation of the source-drain current can thus easily be measured, and the obtained concentration measurement is reliable.

According to another feature of the present invention, the ratio between the respective thicknesses of insulating layer 23 and of gate insulator 34 is selected to be as high as possible. As an example, the ratio ranges between 2 and 20, preferably between 8 and 10. The gate voltage of the transistor will be more sensitive to a variation of the voltage induced by the pairing of molecules 37 with bonds 35 than to a variation of bias voltage $V_p$. A small variation of voltage $V_p$ has little influence upon the source-drain current. The noise on the current measurement due to voltage $V_p$ is attenuated. As an example, the thickness of insulating layer 23 ranges between 5 and 50 nm, preferably between 15 and 25 nm.

According to another feature of the present invention, the thickness of channel region 30 is small. Thus, the capacitive coupling between the upper gate and the lower gate is strong. A variation of the number of charges on the upper gate thus effectively impacts the forming of the channel between the source and the drain under the effect of the biasing of the lower gate. As an example, the thickness of channel region 30 preferably ranges between 1 and 40 nm, preferably between 2 and 20 nm.

To obtain such a thickness of the channel region, an SOI type substrate is advantageously used. The single-crystal silicon channel region provides a better conductivity of the transistor and therefore a better sensitivity of the detector.

Also, when using an SOI type substrate, the thicknesses of the upper and lower gate insulators are very small, i.e. smaller than 60 nm. Thus, the sensitivity of the detector is improved.

By selecting an insulating layer 23 thicker than insulating layer 34, a variation in the number of charges in channel region 30 will be detected and amplified by a variation of the gate voltage on gate 32, which will be smaller than the variation of the gate voltage on gate 25, due to the capacitive coupling between respective upper and lower gates 32 and 25.

Figure 3:
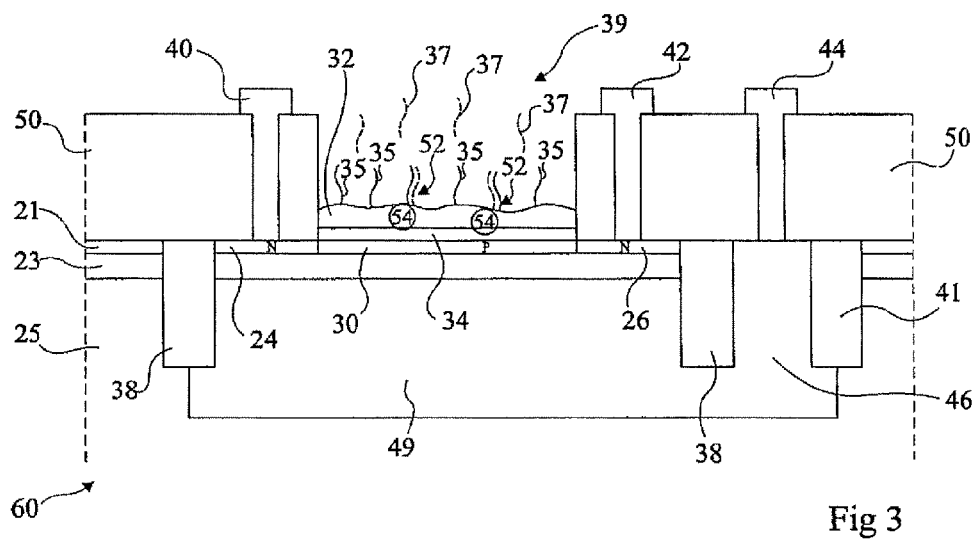
FIG. 3 is a simplified cross-section view of a detector according to another embodiment of the present invention.

FIG. 3 shows a detector 60 corresponding to a practical embodiment of detector 20. MOS transistor 24-30-26 is surrounded with an insulating trench 38, for example, of silicon oxide. Trench 38 crosses thin silicon film 21, insulating layer 23, and penetrates into wafer 25. Trench 38 is sufficiently deep to insulate detector 60 from an adjacent detector. As an example, the depth of the trench may range between 200 and 400 nm, preferably between 250 and 350 nm.

The lower insulated gate is formed of a portion of trench 25 arranged in a well 49. To provide an efficient biasing of the lower insulated gate, the well is advantageously heavily doped. Electrode 44 is connected to well 49 by a sink 46 arranged between insulating trench 38 and an adjacent insulating trench 41. Electrodes 40, 42, and 44 are on the one hand insulated from one another and on the other hand insulated from medium 39 by the presence of an insulator layer 50. As an example, these electrodes may be made of tungsten or aluminum.

As a variation, if trench 25 is heavily doped, it may be provided to bias the lower gate from the rear surface.

An example of a manufacturing method according to an embodiment of the present invention may be the following.

Insulation trenches 38 and 41 crossing silicon layer 21 and insulating layer 23 and penetrating into trench 25 are formed on an SOI-type substrate.

Well 49 is formed by deep ion implantation.

To form sink 46 delimited by the two trenches 38 and 41, silicon film 21 and underlying insulating layer 23 are successively etched. Sink 46 is filled with silicon, for example, by epitaxy. This last step is optional, since the contact can be made directly at the bottom of the etched sink.

Upper gate insulator 34, which may, for example, be silicon oxide or hafnium oxide, is then deposited.

Upper insulated gate 32 is then deposited, after which source and drain regions 24 and 26 are implanted, to form, for example, an N-channel MOS transistor.

After both the drain and source regions and sink 46 have been silicided, electrodes 40, 42, and 44 are formed in insulator layer 50.

The shown MOS transistor has an N-type channel in a P-type well. As a variation, a P-channel transistor may be provided.

A variation of the method comprises forming a sacrificial gate and forming the detector as far as the forming of electrodes 40, 42, and 44. The sacrificial layer is then removed and final gate 32 is then deposited in the cavity. The material forming gate 32 is functionalized to react with the environment. Thus, the molecules forming the material are not degraded by the various steps especially specific to the forming of the source and drain regions of the transistor.

A plurality of detectors 60 may be assembled in an array. In a given array, several sets of detectors may be provided, each of these sets only comprising detectors provided with a given detection layer. Several types of molecules present in a medium can thus be detected.

Specific embodiments of the present invention have been described. Different variations and modifications will occur to those skilled in the art. In particular, an embodiment in which the substrate is of silicon on isolator type has been described. Any other type of semiconductor on isolator is appropriate. Further, the substrate may, for example, be a solid substrate of a semiconductor material in which gate insulator layer 23 is formed by a method of SON (Silicon On Nothing) type.

Detector 20 may be used to detect DNA molecules or ions present in a given medium, without this being a limitation.

Various embodiments with different variations have been described hereabove. It should be noted that those skilled in the art may combine various elements of these various embodiments and variations without showing any inventive step.

Such alterations, modifications, and improvements are intended to be part of this disclosure, and are intended to be within the spirit and the scope of the present invention. Accordingly, the foregoing description is by way of example only and is not intended to be limiting. The present invention is limited only as defined in the following claims and the equivalents thereto.

What is claimed is:

1. A detector of at least one biological or chemical material, the detector comprising:
    a MOS transistor having a channel region inserted between an upper insulated gate and a lower insulated gate, the upper insulated gate comprising a detection layer capable of generating a charge at an interface of the upper insulated gate and an upper gate insulator, wherein:
        a thickness of the upper gate insulator is smaller than a thickness of a lower gate insulator;
        the thickness of the upper gate insulator ranges between 0.5 nm and 5 nm; and
        the thickness of the lower gate insulator ranges between 5 nm and 50 nm.

2. The detector of claim 1, wherein a ratio between the thickness of the lower gate insulator and the thickness of the upper gate insulator ranges between 2 and 20.

3. The detector of claim 1, wherein a thickness of the channel region is defined so that the upper and lower insulated gates are capacitively coupled.

4. The detector of claim 1, wherein a thickness of the channel region ranges between 1 nm and 40 nm.

5. The detector of claim 1, wherein the lower insulated gate is electrically connected to a contact electrode arranged on a front surface.

6. The detector of claim 5, having the lower insulated gate formed of a heavily-doped well connected to the contact electrode by a sink.

7. An array of detectors comprising a plurality of detectors according to claim 1.

8. The array of claim 7, wherein at least two detectors of the plurality of detectors comprise a different detection layer.

9. The detector of claim 2, wherein the ratio between the thickness of the lower gate insulator and the thickness of the upper gate insulator ranges between 8 and 10.

10. The detector of claim 1, wherein the thickness of the upper gate insulator ranges between 2 nm and 3 nm.

11. The detector of claim 1, wherein the thickness of the lower gate insulator ranges between 15 and 25 nm.

12. The detector of claim 4, wherein the thickness of the channel region ranges between 2 nm and 20 nm.

13. The detector of claim 1, wherein the detector detects presence of the at least one biological or chemical material in an environment.

14. The detector of claim 1, wherein the detector is arranged in the environment.

15. The detector of claim 1, wherein the at least one biological or chemical material comprises at least one DNA molecule.

16. A system comprising:
    at least one detector of at least one biological or chemical material, the at least one detector comprising:
        a MOS transistor having a channel region inserted between an upper insulated gate and a lower insulated gate, wherein:
            the upper insulated gate comprises a detection layer capable of generating a charge at an interface of the upper insulated gate and an upper gate insulator;
            a thickness of the upper gate insulator being smaller than a thickness of a lower gate insulator;
            the thickness of the upper gate insulator ranges between 0.5 nm and 5 nm; and
            the thickness of the lower gate insulator ranges between 5 nm and 50 nm.

17. The system of claim 16, wherein a ratio between the thickness of the lower gate insulator and the thickness of the upper gate insulator ranges between 2 and 20.

18. The system of claim 16, wherein a thickness of the channel region is defined so that the upper and lower insulated gates are capacitively coupled.

19. The system of claim 16, wherein a thickness of the channel region ranges between 1 nm and 40 nm.

20. The system of claim 16, wherein the lower insulated gate is electrically connected to a contact electrode arranged on a front surface.

21. The system of claim 20, having the lower insulated gate formed of a heavily-doped well connected to the contact electrode by a sink.

22. The system of claim 16, wherein the at least one detector comprises a plurality of detectors.

23. The system of claim 22, wherein at least two detectors of the plurality of detectors comprise respective different detection layers.

24. A detector for detecting at least one molecule, the detector comprising:
    an upper insulated gate comprising a detection layer for detecting the at least one molecule;
    an upper gate insulator adjacent to the upper insulated gate;
    a channel region arranged between the upper gate insulator and a lower gate insulator; and
    the lower gate insulator; wherein:
        the thickness of the upper gate insulator ranges between 0.5 nm and 5 nm; and
        the thickness of the lower gate insulator ranges between 5 nm and 50 nm.

25. The detector of claim 24, wherein:
    the at least one molecule comprises at least one chemical molecule.

26. The detector of claim 24, wherein:
    the at least one molecule comprises at least one biological molecule.

27. The detector of claim 24, wherein:
    the at least one molecule comprises at least one DNA molecule.

28. The detector of claim 24, wherein:
    the detection layer is capable of generating a charge at an interface of the upper insulated gate and the upper gate insulator.

29. The detector of claim 24, wherein:
    a thickness of the upper gate insulator is smaller than a thickness of the lower gate insulator.

30. The detector of claim 24, further comprising:
    a lower insulated gate adjacent to the lower gate insulator.

31. The detector of claim 30, wherein a thickness of the channel region is defined so that the upper and lower insulated gates are capacitively coupled.

32. The detector of claim 30, wherein the lower insulated gate is electrically connected to a contact electrode.

33. The detector of claim 24, wherein the lower gate insulator is formed in a silicon-on-isolator (SOI) substrate.

* * * * *

UNITED STATES PATENT AND TRADEMARK OFFICE
CERTIFICATE OF CORRECTION

PATENT NO. : 8,878,258 B2  Page 1 of 1
APPLICATION NO. : 12/914033
DATED : November 4, 2014
INVENTOR(S) : Stéphane Monfray et al.

It is certified that error appears in the above-identified patent and that said Letters Patent is hereby corrected as shown below:

On the title page

Item (73):
"STMicroelectronics (Crolle 2) SAS, Crolles (FR)" is incorrect. The correct item should read,
--STMicroelectronics (Crolles 2) SAS, Crolles (FR)--.

Signed and Sealed this
Twenty-ninth Day of March, 2016

Michelle K. Lee
*Director of the United States Patent and Trademark Office*